US010815361B2

(12) United States Patent
Magnusson et al.

(10) Patent No.: US 10,815,361 B2
(45) Date of Patent: Oct. 27, 2020

(54) NON-PHTHALIC PLASTICISER

(71) Applicant: PERSTORP AB, Perstorp (SE)

(72) Inventors: Anders Magnusson, Bjarnum (SE); Hakan Bjornberg, Angelholm (SE); Niklas Persson, Hoganas (SE); Maria Peterson, Hoor (SE); Kent Sorensen, Perstorp (SE)

(73) Assignee: PERSTORP AB, Perstorp (SE)

( * ) Notice: Subject to any disclaimer, the term of this patent is extended or adjusted under 35 U.S.C. 154(b) by 484 days.

(21) Appl. No.: 15/281,638

(22) Filed: Sep. 30, 2016

(65) Prior Publication Data

US 2017/0096543 A1   Apr. 6, 2017

Related U.S. Application Data

(63) Continuation-in-part of application No. 13/818,036, filed as application No. PCT/SE2011/000138 on Jul. 26, 2011, now abandoned.

(30) Foreign Application Priority Data

Aug. 23, 2010   (SE) ..................................... 1000853

(51) Int. Cl.
| | |
|---|---|
| *C08K 5/103* | (2006.01) |
| *C08K 5/11* | (2006.01) |
| *C08K 5/1535* | (2006.01) |
| *C07C 69/34* | (2006.01) |
| *C08J 3/18* | (2006.01) |
| *C08K 5/12* | (2006.01) |
| *C08K 5/092* | (2006.01) |
| *C07C 69/33* | (2006.01) |

(52) U.S. Cl.
CPC .............. *C08K 5/103* (2013.01); *C07C 69/33* (2013.01); *C07C 69/34* (2013.01); *C08J 3/18* (2013.01); *C08K 5/092* (2013.01); *C08K 5/11* (2013.01); *C08K 5/12* (2013.01); *C08K 5/1535* (2013.01)

(58) Field of Classification Search
CPC ......... C08K 5/103; C08K 5/11; C08K 5/1535
USPC ......................................................... 524/284
See application file for complete search history.

(56) References Cited

U.S. PATENT DOCUMENTS

| | | | |
|---|---|---|---|
| 2,760,632 A | | 8/1956 | Hillyer |
| 2,815,327 A | * | 12/1957 | Dick ................... C10M 169/04 252/402 |
| 3,041,369 A | | 6/1962 | Samuel |
| 3,670,013 A | | 6/1972 | Leibfried et al. |
| 5,356,981 A | * | 10/1994 | Tsuruga ................... C08K 3/20 423/420.2 |
| 5,430,108 A | * | 7/1995 | Schlosberg ............. C07C 69/33 524/310 |
| 5,430,180 A | | 7/1995 | Schlosberg et al. |
| 5,886,072 A | | 3/1999 | Leonard et al. |
| 2007/0227652 A1 | | 10/2007 | Kawabe et al. |

FOREIGN PATENT DOCUMENTS

| | | | |
|---|---|---|---|
| EP | 0514988 A2 | | 11/1992 |
| GB | 884660 | * | 12/1961 |
| GB | 884660 A | | 12/1961 |
| WO | WO-0100722 A1 | | 1/2001 |
| WO | WO 03/014220 | * | 2/2003 |

OTHER PUBLICATIONS

Richard J. Lewis, Sr., Hawley's Condensed Chemical Dictionary, 1997 by Van Nostrand Reinhold, Thirteenth Edition, pp. 909 and 1171.*
Richard J. Lewis, Sr., Hawley's Condensed Chemical Dictionary, Copyright 1997 by Van Nostrand Reinhold, Thirteenth Edition, p. 908.*
Sanderson et al., Synthesis and Evaluation of Dialkyl Furan-2,5-Dicarboxylates as plasticizers for PVC, Department of Chemistry and Institute for Polymer Science, p. 1785 . . .
International Search Report, PCT/SE2011/000138.
Annex to the Communication dated Apr. 19, 2018 for corresponding EP Application No. 11 820 250.6.
H.K. Shobha et al., "Structural expressions of ling-chain esters on their plasticizing behavior in poly(vinyl chloride)", Macromolecules, vol. 25, No. 25, 1992, pp. 6765-6769.
Hosadurga K. Shobha et al., "Structural dependence of density in high molecular weight esters", Journal of Chemical and Engineering Data, vol. 37, No. 4, 1992, pp. 371-376.
Tai S. Chao et al., "Esters from branched-chain acids and neopentylpolyols and phenols as base fluids for synthetic lubricants", Industrial & Engineering Chemistry Product Research and Development, vol. 22, No. 2, 1983, pp. 357-362.
Keshavaraj, R. et al., "Neural-Network-Based Model Approach for Density of High-Molecular-Weight Esters Used as Plasticizers", Advances in Polymer Technology, Wiley and Sons, Hoboken, NJ, US, vol. 14, No. 3, 1995, pp. 215-225.
Kishore, K. et al., "Plasticization phenomena and fire retardancy in PVC", Indian Journal of Chemistry, vol. 31 A, 1992, pp. 590-595.
Sanderson, R.D. et al., "Synthesis and Evaluation of Dialkyl Furan-2,5-Dicarboxylates as Plasticizers for PVC", Journal of Applied Polymer Science, Wiley, US, vol. 53, No. 13, 1994, pp. 1785-1793.

* cited by examiner

*Primary Examiner* — Deve V Hall
(74) *Attorney, Agent, or Firm* — Polsinelli PC

(57) ABSTRACT

The present invention refers to a method for producing a low-emitting plasticised polyvinylchloride composition, having a fusion time of less than 5.50 s and a volatility of less than 10% weight loss, by mixing pentaerythritol tetravalerate with a polyvinylchloride composition, the fusion time being measured according to DIN 54 802 and ISO/DIS 4574 and the volatility being measured according to ISO 176 Method A. In a further aspect the present invention refers to a thermoplastic article suitable for use in environments where the article is exposed to heat, wherein the thermoplastic article is based on a plasticized polyvinylchloride composition produced by the method of the present invention.

17 Claims, 6 Drawing Sheets

NON-PHTHALIC PLASTICISER

CROSS REFERENCE TO RELATED APPLICATIONS

This application is a Continuation-In-Part of U.S. patent application Ser. No. 13/818,036, filed Jan. 16, 2015, which is a 35 U.S.C. 371 National Stage entry of International patent Application Serial No. PCT/SE2011/000138 Filed Jul. 26, 2011, claiming benefit of Swedish patent application serial number 10008530, filed Aug. 23, 2010, the entire disclosures of which are herein incorporated by reference in their entireties.

BACKGROUND OF THE INVENTION

1. Field of the Invention

The present invention refers to a plasticiser, said plasticiser being an ester formed by reaction of a polyol and a monocarboxylic acid, preferably having 4-5 carbon atoms. In a further aspect the present invention refers to the use of said plasticiser in a PVC resin.

2. Description of the Related Art

Plasticisers have the ability to reduce the glass transition temperature of polymers and thereby provide soft and/or flexible products, contrary to the hard and brittle basic material. Organic esters constitute the major group of poly (vinyl chloride) (PVC) plasticisers. Among these organic esters phthalates are without competition the largest subgroup. The most commonly used phthalate esters as PVC plasticisers are di-2-ethylhexyl phthalate (DEHP), also known as dioctyl phthalate (DOP), diisononyl phthalate (DINP) and diisodecyl phthalate (DIDP). Further examples of organic esters used as PVC plasticisers are adipates, trimellitates, sebacates and azelates. Phosphate esters, such as tris (2-ethylhexyl) phosphate, and sulphonate esters, such as arylesters of sulphonic acids, are used in minor amounts. The preparation and the use of said plasticisers are well known and thoroughly disclosed in a number of handbooks and encyclopedias of chemical technology.

Plasticized PVC is used in a multitude of plastic items going to a multitude of end-user sectors such as flexible films, cables and wires, flooring, flexible tubes and profiles and coated fabric and paper. Over the last few decades, the use of plastics as packaging materials has increased due to their properties and processability. As a result of contact between packed food and plastics, traces of plasticisers may migrate into the food contaminating it and affecting consumers' health. The situation has created an increasing desire for phthalate-free plasticisers for applications like toys, food contact materials, medicals and other applications where the use of phthalates are either restricted or non-wanted by end-users.

Di-2-ethyl hexyl phthalate (DEHP) is often called dioctyl phthalate and abbreviated DOP. It is the most important phthalate, being the diester of phthalic acid and 2-ethylhexanol. Due to its suitable properties and the low cost, DOP is widely used as a plasticiser in PVC articles. Plastics may contain 1% to 40% of DOP. Both technically and commercially it is the reference against which other plasticisers are assessed. DOP is used in nearly all application areas for plasticised PVC. Technical limits on its use are imposed by considerations of volatility and migration. DOP is associated with health risks since it has a low vapour pressure and the temperatures for processing PVC articles are often high, leading to release of high levels. DOP can be absorbed from food and water. It can also leach into a liquid that comes in contact with the plastic.

On 28 Oct. 2008, the European Chemicals Agency published a list of the first substances to enter onto the REACH authorisation "candidate list". As expected, three phthalates, di-2-ethylhexyl phthalate (DEHP or DOP), di-n-butyl phthalate (DBP) and butyl benzyl phthalate (BBP), were included on the list due to their EU hazard classification. The inclusion of DEHP, DBP and BBP on the "candidate list" for authorisation means that any supplier of an article containing more than 0.1% weight by weight (w/w) of them now has an obligation to provide information to the recipient of that article. Further down the supply chain, retailers also have an obligation to provide the same information to consumers, but only if a consumer requests it. According to the general view non-labelled phthalates (for instance DINP, DIDP and DPHP (dipropylheptyl) phthalate) will take over after DOP and other labelled phthalates. Long term risk assessment studies in the European Union have largely cleared DINP and DIDP and they are viewed as cost-effective substitutes to DOP. However, non-labelled phthalates are represented by the bad press surrounding the name "phthalates".

Various alternative plasticisers such as adipates, trimellitates, citrates, benzoates esters, "bioplasticisers" have been evaluated, but none being currently viewed as "the" substitute for commercial phthalates. They are mostly hindered by a high price as well as in some cases poorer performance. The situation has created a market desire for a competitively priced, well performing, environment-friendly non-phthalic plasticiser.

One of the most widely used phthalate substitute today is Hexamoll® DINCH (BASF's tradename for 1,2-cyclohexane dicarboxylic acid diisononyl ester). Hexamoll® DINCH (in the following text denoted DINCH) is a non-phthalic plasticiser that has been developed for the manufacture of flexible plastic articles in sensitive application areas such as toys, medical devices and food packaging. From a chemical point of view it belongs to the group of aliphatic esters.

Aliphatic esters of polyfunctional alcohols exhibit a number of advantages compared to for example aromatic esters, such as above phthalates constituting the majority of plasticisers used today. The aliphatic structure implies the possibility of improved stability towards outdoor exposure. Furthermore, they exhibit a reduced tendency to generate fire smoke. Said aliphatic esters also exhibit, when raw materials are properly chosen, a reduced volatility and are hence emitted to the environment in lower amounts. Said esters often exhibit an increased biodegradability compared to aromatic esters, like phthalates, why the environmental impact is reduced. Aliphatic esters are further judged to have less impact on living organisms than phthalates. This type of esters has due to high thermal and oxidation stability as well as due to said biodegradability a long time use in lubricants. Said esters have, however, a limited use as plasticisers mainly because of their limited compatibility with PVC. U.S. Pat. No. 3,939,201 teaches triesters of triethanolmethane and an acid component consisting of a monocarboxylic acid preferably having 6-8 carbon atoms such as the exemplified 2-ethylhexanoic acid. European Patent No. 0739377 teaches a plasticised PVC composition consisting essentially of a mixture of C5 and C7 alkyl carboxylic acids and 3,5,5-trimethylhexanoic acid. The International Patent Application No. 01/00722 relates to a plasticiser for polymeric composition, preferably PVC. The plasticiser comprises at least one polyolester obtainable by addition of at least one aromatic monocarboxylic acid and/or at least one aliphatic monocarboxylic acid having 2-5 carbon atoms and at least one aliphatic monocarboxylic acid having 6-12 carbon atoms to an aliphatic polyalcohol having three or more hydroxyl groups. European Patent No. 1353988 discloses the use of a trimethylolpropane ester-based multi-component composition as plasticiser.

SUMMARY OF THE INVENTION

An aliphatic ester according to the present invention has shown to be a very well performing non-phthalic plasticiser for PVC. Better than commercial non-phthalic plasticisers like DINCH and in several aspects even better than phthalates like DOP, DPHP and DINP. In comparison with DINCH, DOP, DPHP and DINP the plasticiser of the present invention has proven to be a more efficient PVC plasticiser. The fusion time is shorter, i.e. the compatibility with PVC is higher and the plasticising effect is higher, i.e. the same plasticising effect can be obtained with a smaller amount of plasticiser. Migration and chemical resistance are also significantly improved relative to the phthalates and DINCH. The present invention thus provides a more efficient and environmental-friendly alternative to the commercial phthalic PVC plasticizers mentioned above and the commercial non-phthalic PVC plasticizer DINCH.

The present invention accordingly refers to a plasticiser, said plasticiser being an ester formed by reaction of a polyol and a monocarboxylic acid. Said ester has a general formula (1) of

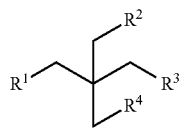

(1)

wherein, $R^1$, $R^2$, $R^3$ and $R^4$ represent —O—CO-alkyl groups containing 4-5 carbon atoms.

Said —O—CO-alkyl group is butyrate, valerate or a mixture thereof. In one embodiment of the present invention at least one of said —O—CO-alkyl groups is butyrate. In another embodiment of the present invention at least two of said —O—CO-alkyl groups are butyrates and in yet another embodiment at least three of said —O—CO-alkyl groups are butyrates.

DETAILED DESCRIPTION OF THE PREFERRED EMBODIMENTS

Figure 1:
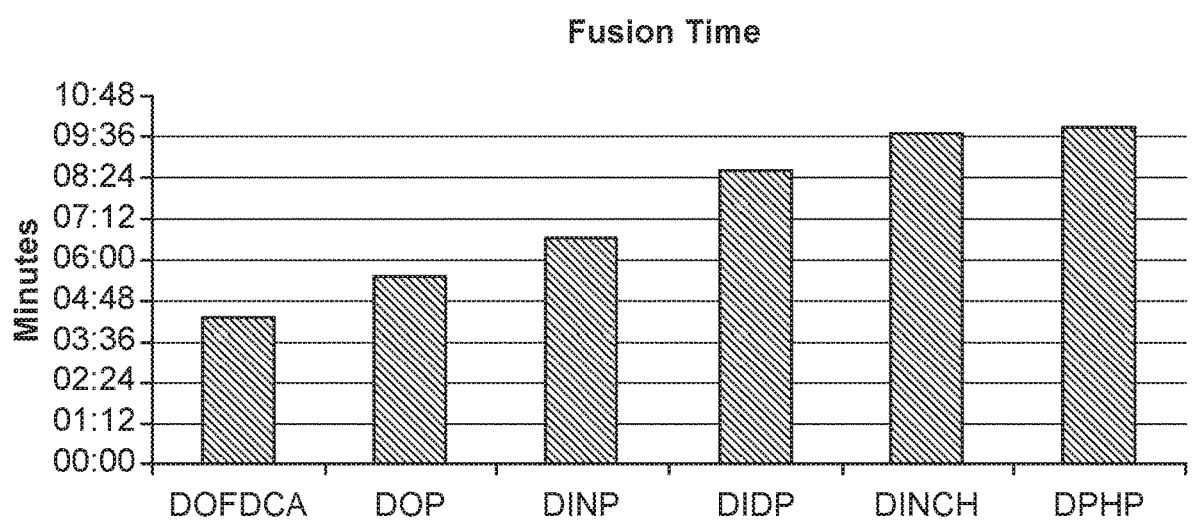
FIG. 1 is a graphical representation of fusion time (in minutes) for various plasticizers.

The plasticiser of the present invention is preferably an ester formed by reaction of pentaerythritol and a monocarboxylic acid. Said monocarboxylic acid preferably being butyric or valeric acid.

One problem with using butyrates is the potent smell of butyric acid during processing. However, once surplus of butyric acid is removed from the plasticiser, the smell is reduced. It has also been found that a PVC plastisol comprising polyol butyrates according to the invention did not produce any unpleasant smell under normal conditions. We have quite surprisingly found that a pentaerythritol ester having one, two or three groups of butyrate while the remaining groups are valerate indeed did smell much less than expected during processing.

It is, according to one embodiment of the invention, possible to esterify in two steps, first adding and reacting the butyric acid with pentaerythritol in the desired molar ratio of the finished product and in a second step add the valeric acid in surplus. This way any smell from non-reacted butyric acid will be minimised.

It has, during experimentation with the plasticisers according to the invention been found that the fusion time is very short, while quite surprisingly, the volatility is still in parity and in some cases lower than commercially available plasticisers. The short fusion time implies that the processing time and/or temperature during agglomeration of plasticiser can be lower wherein the problem with smell during processing becomes even less significant.

Tests were also performed with trimethylolpropane trivalerate (TMP-V) which showed to be very volatile. A common problem with volatility of plasticisers not many are aware of is fogging on windshields in cars. The dashboard often becomes hot, causing the plasticiser to evaporate and set as a film on the inside of the windshield. This film is often rather difficult to remove and will, with time, become a traffic hazard due to impaired visibility, especially in low light conditions and when the sun is close to horizon. It has shown that TMP-V does have very limited use due to its volatility.

The present invention further refers to the use of said plasticiser in a PVC resin. Pentaerythritol adipate can preferably be used as a co-stabiliser in such a resin.

According to a special embodiment of the invention, a plasticiser blend comprising 1-20 parts by weight of a plasticiser being an ester formed by reaction of pentaerythritol and a monocarboxylic acid being butyric or valeric acid which is blended with 1-20 parts by weight of an oligo ester of 2-ethylhexanol and furandicarboxylic acid. The plasticiser blend suitably comprises 1-5 parts by weight of the pentaerythritol ester blended with 1-5 parts of the oligo ester of 2-ethylhexanol and furandicarboxylic acid. Preferably the plasticiser blend comprises 1-2 parts by weight of the pentaerythritol ester blended with 1-2 parts by weight of the oligo ester of 2-ethylhexanol and furandicarboxylic acid.

The present invention refers to a method for producing a low-emitting plasticised polyvinylchloride composition, having a fusion time of less than 5.50 s and a volatility of less than 10% weight loss, by mixing pentaerythritol tetravalerate with a polyvinylchloride composition, said fusion time being measured according to DIN 54 802 and ISO/DIS 4574 and said volatility being measured according to ISO 176 Method A. Said plasticized polyvinylchloride composition comprises at least 20% by weight of pentaerythritol tetravalerate and preferably at least 30% by weight of pentaerythritol tetravalerate.

Said plasticized polyvinylchloride composition may also comprise an oligo ester of 2-ethylhexanol and furandicarboxylic acid. According to one embodiment of the invention said plasticized polyvinylchloride composition also comprises pentaerythritol adipate.

The present invention further refers to a thermoplastic article suitable for use in environments where it is exposed to heat, wherein the thermoplastic article is based on a plasticized polyvinylchloride composition produced by the method of the present invention. The thermoplastic article of the invention is a foil, film or molded polyvinylchloride article, for instance a low-fogging dashboard for cars.

EXAMPLES

The present invention is further explained with reference to enclosed embodiment Examples, which are to be construed as illustrative and not limiting in any way.

Example 1a illustrates the preparation of an ester of the present invention: pentaerythritol tetra n-butyrate.

Example 1b illustrates the preparation of an ester of the present invention: pentaerythritol tetra i-butyrate.

Example 1c illustrates the preparation of an ester of the present invention: pentaerythritol tri n-butyrate, mono-valerate.

Example 1d illustrates the preparation of an ester of the present invention: pentaerythritol di n-butyrate, di-valerate.

Example 2 illustrates the preparation of an ester of the present invention: pentaerythritol tetravalerate.

Example 3a illustrates the preparation of an ester according to a special embodiment of the present invention: DOFDCA.

Example 3b illustrates the preparation of a plasticiser blend according to a special embodiment of the present invention: pentaerythritol tetra n-butyrate and DOFDCA.

Example 4 illustrates the preparation of plasticised PVC sheets.

Example 5 illustrates the evaluation of obtained plasticised PVC sheets.

Example 1a

Synthesis of Pentaerythritol Tetra n-Butyrate 2 mole of monopentaerythritol and 8 mole (+25% surplus) of n-butyric acid were charged into a glass reactor equipped with stirrer, condenser, nitrogen inlet and thermometer. 4% by weight of xylene was added as an azeotropic solvent. The mixture was heated under stirring to 220° C. Esterification water began to evaporate and when approximately 80% of a theoretical water amount had been collected the reaction mixture was cooled to 150° C. and 0.1% by weight of titanium(IV)isopropoxid (Tyzor TPT) was added as a catalyst. The mixture was subsequently heated to 220° C. and maintained until a desired acid number was reached and a theoretical water amount was collected, where after the reaction mixture was cooled and the solvent and unreacted n-butyric acid was removed under vacuum while slowly increasing the temperature to 180° C. After cooling, the solution was neutralised by addition of calcium hydroxide and a small amount of water, followed by vacuum distillation at 140° C. and filtration at room temperature. Pentaerythritol butyrate with 94% tetra esterification was obtained.

Example 1b

Synthesis of Pentaerythritol Tetra i-Butyrate

The synthesis where performed as in example 1a with the difference that n-butyric acid was replaced by i-butyric acid.

Example 1c

Synthesis of Pentaerythritol 1 Tri n-Butyrate Mono-Valerate

The synthesis where performed as in example 1a with the difference that 6 mole of n-butyric acid and 2 mole of valeric acid were blended before being charged into the glass reactor.

Example 1d

Synthesis of Pentaerythritol Di n-Butyrate Di-Valerate

The synthesis where performed as in example 1a with the difference that 4 mole of n-butyric acid and 4 mole of valeric acid were blended before being charged into the glass reactor.

Example 2

Synthesis of Pentaerythritol Tetravalerate 2 mole of monopentaerythritol and 8 mole (+25% surplus) of valeric acid were charged into a glass reactor equipped with stirrer, condenser, nitrogen inlet and thermometer. 4% by weight of xylene was added as an azeotropic solvent. The mixture was heated under stirring to 220° C. Esterification water began to evaporate and when approximately 80% of a theoretical water amount had been collected the reaction mixture was cooled to 150° C. and 0.1% by weight of titanium(IV)isopropoxid (Tyzor TPT) was added as a catalyst. The mixture was subsequently heated to 220° C. and maintained until a desired acid number was reached and a theoretical water amount was collected, where after the reaction mixture was cooled and the solvent and unreacted valeric acid was removed under vacuum while slowly increasing the temperature to 180° C. After cooling, the solution was neutralised by addition of calcium hydroxide and a small amount of water, followed by vacuum distillation at 140° C. and filtration at room temperature. Pentaerythritol valerate with 97% tetra esterification was obtained.

Example 3a

Synthesis of DOFDCA According to a Special Embodiment of the Invention

In a 700 ml round bottom glass flask equipped with an agitator, condenser, Dean-Stark separator and inert gas inlet, was charged 125 g of 2-ethylhexanol, 50 g of furandicarboxylic acid (FDCA) and 0.07 g of tetraisopropyltitanate as catalyst. The reaction mixture was during 150 minutes heated to reflux at 195° C. The temperature was slowly increased to 215° C. while maintaining a good reflux. When the acid number was 0.3 mg KOH/g the solution was cooled, vacuum applied and excess of 2-ethylhexanol distilled off. Subsequently a small portion of water was added, when the temperature was below 100° C., to destroy the catalyst. The reaction product was neutralised using a base in excess to residual acid value. Vacuum was once more applied and residual volatile compounds were distilled off at 150° C. during one hour. The reaction product, an oligoester plasticiser, was finally cooled to room temperature.

Yielded oligo ester plasticiser exhibited following properties:

| | |
|---|---|
| Diester content, %: | 99.5 |
| Monoester content, %: | 0.2 |
| 2-Ethylhexanol content, %: | 0.02 |
| FDCA content, % | <0.02 |
| Acid value, mg KOH/g: | 0.04 |
| Viscosity at 20° C., mPas | 103 |
| Colour, Hazen: | 360 |

Alternative Embodiment Ester

In a 700 ml round bottom glass flask equipped with an agitator, condenser, Dean-Stark separator and inert gas inlet, was charged 170 g of 2-ethylhexanoic acid, 50 g of di(hydroxymethyl)furan, 7 g of xylene as azeotropic solvent and 0.07 g of tetraisopropyltitanate as catalyst. The solution was during 150 minutes heated to reflux. The temperature was subsequently slowly increased to 230° C. while maintaining a good reflux. The reaction product was, when the hydroxyl number was less than 1 mg KOH/g was reached, cooled and vacuum was applied for evaporation of excess 2-ethylhexanoic acid and xylene. A small portion of water was added when the temperature was below 100° C. to destroy the catalyst. The reaction product was neutralised with a base used in an excess to residual acid number. Vacuum was applied and residual volatile compounds were during one hour distilled off at 150° C. Yielded product, an oligoester of plasticiser type, was finally filtered. The oligoester plasticiser was by analysis determined to have a diester content of more than 99%.

The plasticiser (DOFDCA) obtained in Example 3a was evaluated in a PVC composition and compared to the commercially available plasticisers, di-(2-ethylhexyl)phthalate (DOP), di-(2-propylheptyl)phthalate (DPHP), di-(isododecyl)phthalate (DIDP), di-(isononyl)phthalate (DINP) and di-(isononyl)cyclohexanoate (DINCH).

| The PVC composition was: | PVC K-70 (Norvinyl S7060) | 100 phr |
|---|---|---|
| | Plasticiser | 50 phr |
| | Stabiliser Mark CZ 118E | 2 phr | i) The fusion time was evaluated and found to be superior for DOFDCA over the comparative plasticizers, implying improved productivity for the PVC converter. The result is given in FIG. 1.

ii) The hardness was measured as ShoreA hardness according to ASTM D 2240-3 after 1, 7 and 14 days at room temperature and 50% relative humidity. The results below indicate that DOFDCA is the most efficient plasticiser. The result is given in FIG. 2.

Example 3b

Preparation of a Plasticiser Blend According to a Special Embodiment of the Present Invention 1 part per weight of pentaerythritol tetra n-butyrate from example 1a where mixed with 1 part per weight of DOFDCA from example 3a. The mix between pentaerythritol tetra n-butyrate and DOFDCA was fully miscible.

Comparative Example, TMP-V

Synthesis of Trimethylolpropane Trivalerate 2 mole of trimethylolpropane and 6 mole of valeric acid were charged into a glass reactor equipped with stirrer, condenser, nitrogen inlet and thermometer. 4% by weight of heptane and 0.1% of p-toluenesuphonic acid was added as an azeotropic solvent and catalyst respectively. The mixture was heated under stirring to 140° C. Esterification water began to evaporate at 125° C. The temperature was increased to 180° C. in steps until all expected water had evaporated. The reaction was followed until a desired acid number was reached and a theoretical water amount was collected, where after the reaction mixture was cooled and the solvent and unreacted acid was removed under vacuum. The solution was neutralised by addition of calcium hydroxide. Cellite was added and the product was then filtered. Trimethylolpropane trivalerate with 95.7% tri esterification was obtained.

Example 4

Preparation of Plasticised PVC Sheets

PVC resins (suspensions of PVC particles in a plasticiser) of below formulations were prepared:

| | PVC (Norvinyl S-706) (g) | | | | | |
|---|---|---|---|---|---|---|
| | 190.8 | 190.8 | 190.8 | 190.8 | 190.8 | 190.8 |
| Polyolester plasticiser from Example 1a, P-nB (g) | 95.4 | — | — | — | — | — |
| Polyolester plasticiser from Example 1b, P-iB (g) | — | 95.4 | — | — | — | — |
| Polyolester plasticiser from Example 1c, (1:3:1) P-nB-V (g) | — | — | 95.4 | — | — | — |
| Polyolester plasticiser from Example 1d, (1:2:2) P-nB-V (g) | — | — | — | 95.4 | — | — |
| Polyolester plasticiser from Example 2, P-V (g) | — | — | — | — | 95.4 | — |
| Plasticiser blend from example 3b, (1:1) DOFDCA/P-nB | — | — | — | — | — | 95.4 |
| Stabiliser (Mark CZ 118 E) (g) | 3.8 | 3.8 | 3.8 | 3.8 | 3.8 | 3.8 |

| | PVC (Norvinyl S-706) (g) | | | | |
|---|---|---|---|---|---|
| | 190.8 | 190.8 | 190.8 | 190.8 | 190.8 |
| Plasticiser 1 (DPHP) (g) | 95.4 | — | — | — | — |
| Plasticiser 2 (DOP) (g) | — | 95.4 | — | — | — |
| Plasticiser 4 (DINCH) (g) | — | — | 95.4 | — | — |
| Plasticiser 3 (DINP) (g) | — | — | — | 95.4 | — |
| Polyolester plasticiser from comparative example, TMP-V (g) | — | — | — | — | 95.4 |
| Stabiliser (Mark CZ 118 E) (g) | 3.8 | 3.8 | 3.8 | 3.8 | 3.8 |

The components of each PVC resin were carefully mixed and then calendered to a sheet using a two-roll mill at 165° C.

Example 5

Evaluation of the Obtained Plasticised PVC Sheets

All plasticised PVC sheets obtained in Example 4 were evaluated regarding fusion time, hardness, migration, volatility and extraction/absorption in water, heptane and 1% soap solution and yellowness.

Fusion Time
Determination of Hot Plasticizer Absorption (Standard: DIN 54 802 and ISO/DIS 4574)

A test to determine the time required for PVC and plasticiser to completely mix together and form a uniform blend. A mixing bowl was heated to the test temperature of 88° C. and charged with 300 g PVC resin. A stirring of 60 rpm was applied for 5 minutes to allow the resin to reach the bowl temperature. 150 g plasticizer was then added and the time required for PVC and plasticiser to completely mix together and form a uniform blend was measured.

Figure 3A:
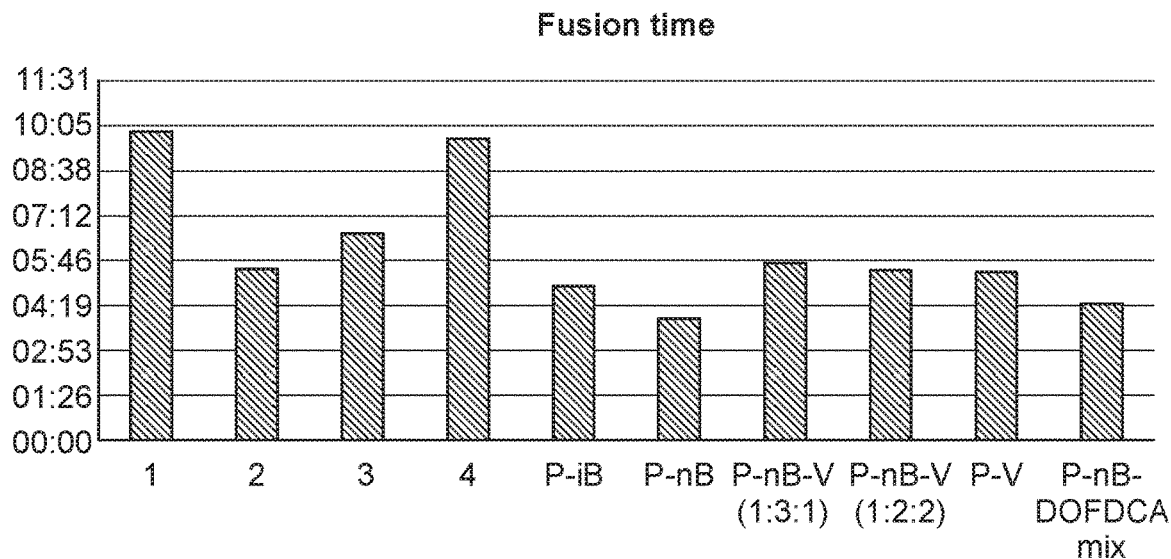
FIG. 3A is a graphical representation of Fusion Time of hot plastizer absorption under standard test.

The results are presented in FIG. 3A.

Hardness
Durometer Hardness Shore A. (Standard: ASTM 2240:3)

A test based on the penetration of a specific type of indentor when forced into the material under specific conditions. The indentation hardness is inversely related to the penetration and dependant on the elastic modulus and viscoelastic behaviour of the material.

Figure 3B:
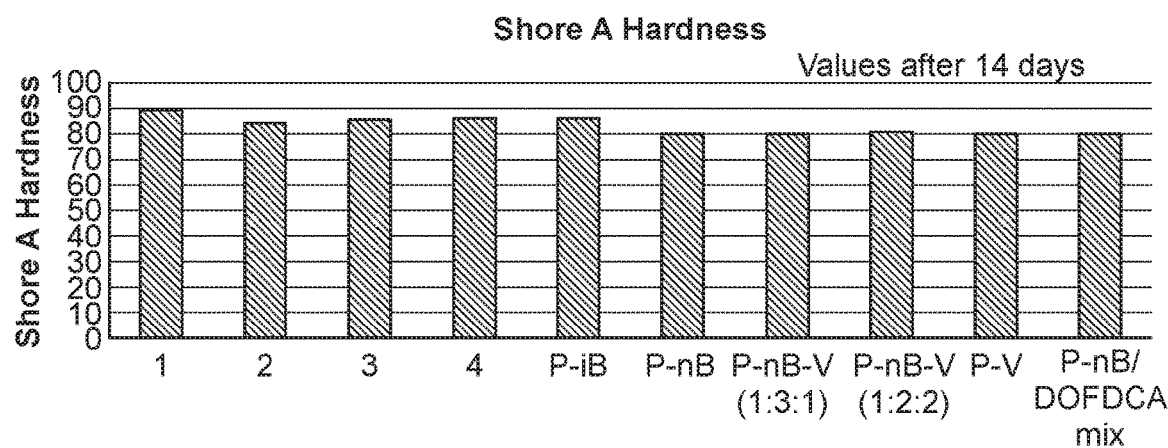
FIG. 3B is a graphical representation of ShoreA Hardness values after 14 days.

The results are presented in FIG. 3B.

Migration
Determination of Migration of Plasticisers (Standard: ISO 177)

A test based on quantitative determination of the loss of mass of a sheet of plasticized plastic placed between two fresh absorbent backing discs. A rubber-PVC-rubber sandwich was wrapped with aluminium foil and rubber sheets before being placed between two glass plates. A weight of 5 kg was placed on the sandwich assembly and the whole package was placed in an oven with a temperature of 70±2° C. The samples were then picked out and the weight of both the plasticized plastic and the absorbent backing discs was measured after 3, 7, 14 and 28 days.

Figure 4A:
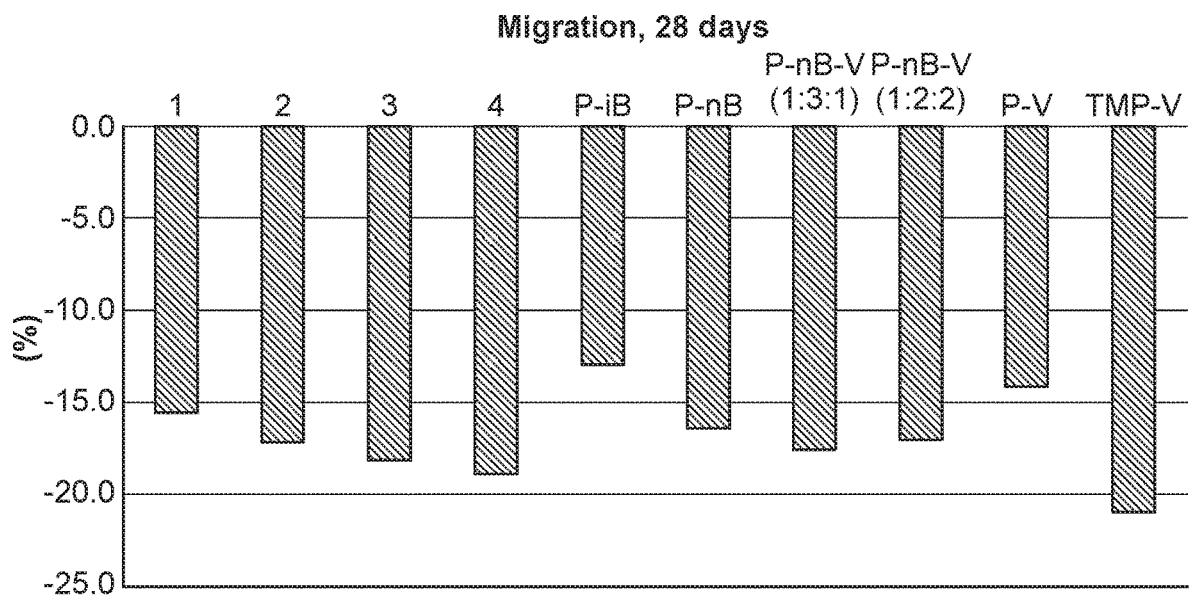
FIG. 4A is a graphical representation of Migration of plastizers at 28 days.

The results for 28 days are presented in FIG. 4A.

Volatility
Activated Carbon Method (Standard: ISO 176 Method A)

A test method based on quantitative determination of the loss of plasticiser from plasticized plastic materials upon heating, where it is generally assumed that no significant amounts of other volatile materials are present. 120 cm$^3$ of activated carbon was spread on the bottom of metal container and a test sample was placed on top of the carbon and covered with another 120 cm$^3$ of activated carbon. Two further samples were placed in the container, each covered with 120 cm$^3$ of carbon, where after the container was sealed with a lid. The container was placed in oven with a temperature of 100±1° C. The activated carbon surrounding the samples absorbed the plasticiser extracted upon heating. After 7 days the container was removed from the oven and cooled to room temperature. The samples were removed from the container, carefully brushed free from carbon particles and weighed.

Figure 4B:
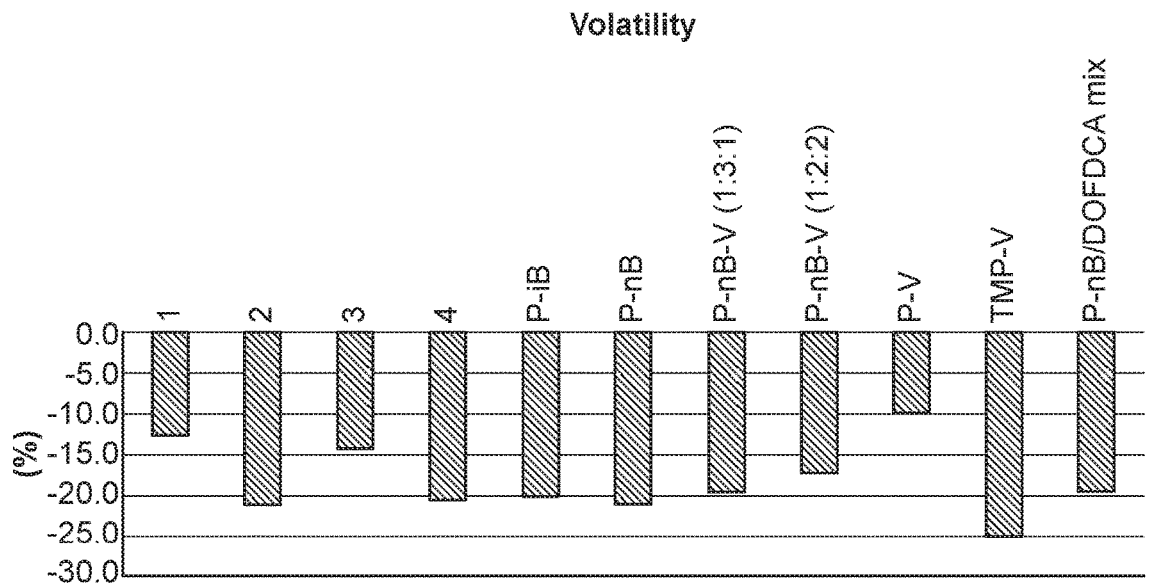
FIG. 4B is a graphical representation of Volatility after 7 days.

The results are presented in FIG. 4B.

Absorption and Extraction
Determination of absorption and extraction of water, heptanes and 1% soap.

A test method based on quantitative determination of the loss of mass of plasticized plastic sheet completely immersed in the test liquid for a specified time and at specified temperature. The weight of the plasticized plastic sheets was determined before immersion, after removal from the liquid and after drying. The samples were immersed for 1 day in water and 1% soap solution at 70° C. The samples were also immersed in heptane for 1 day at 23° C. The extracted samples were wiped dry, where after the mass loss was determined.

Figure 5A:
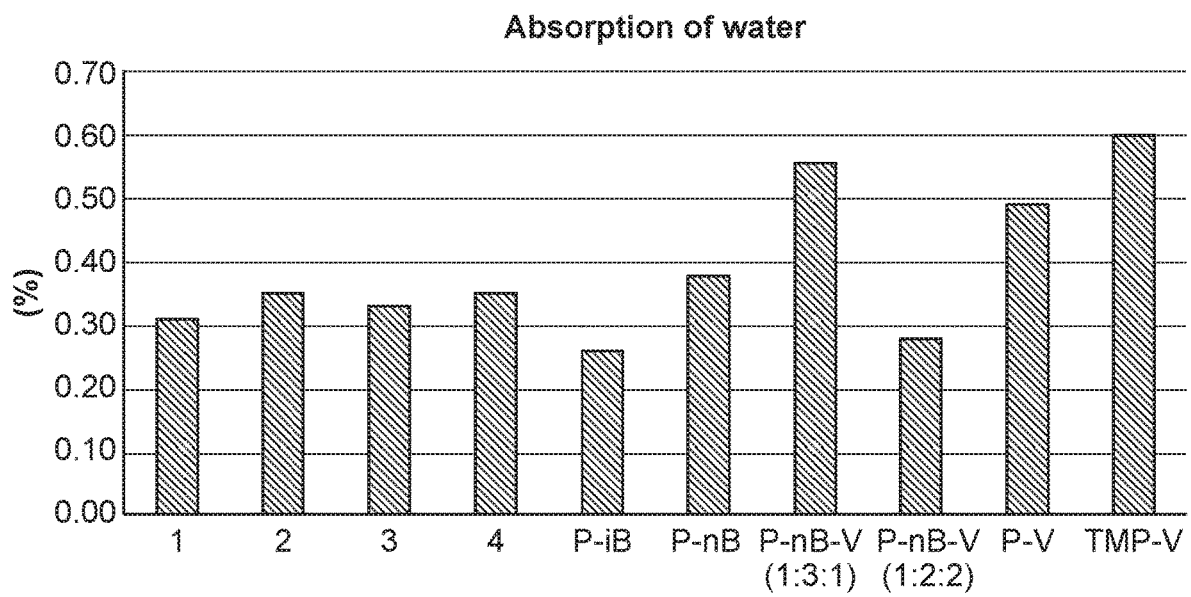
FIG. 5A is a graphical representation of absorption and extraction of water after 1 day.
Figure 5B:
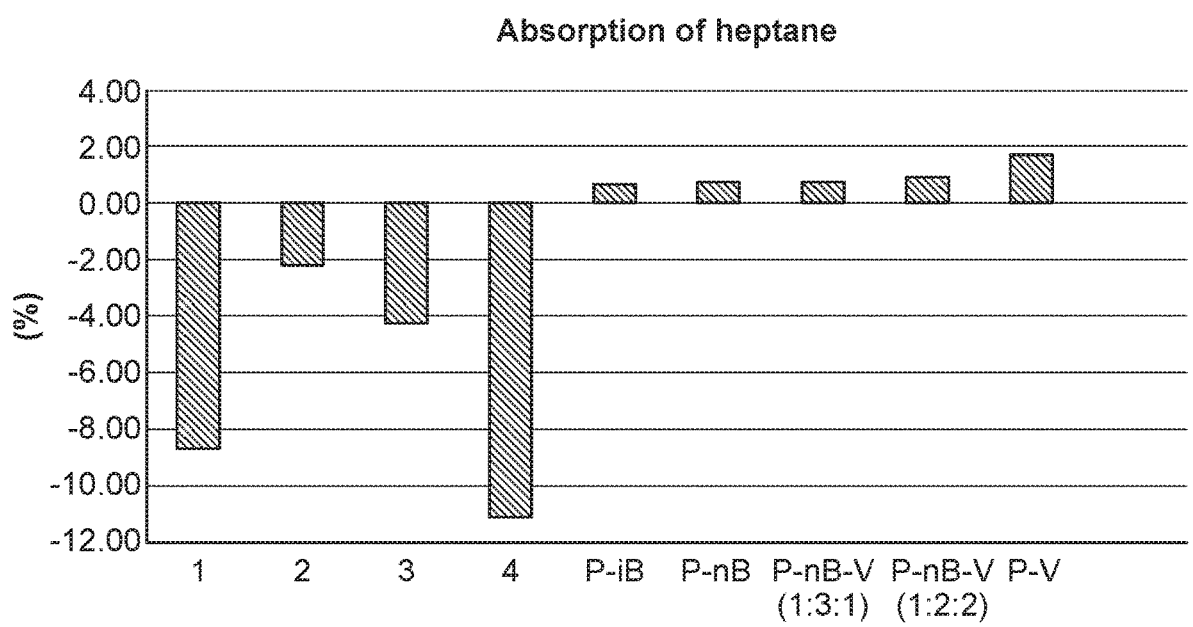
FIG. 5B is a graphical representation of absorption and extraction of heptanes after 1 day.
Figure 6:
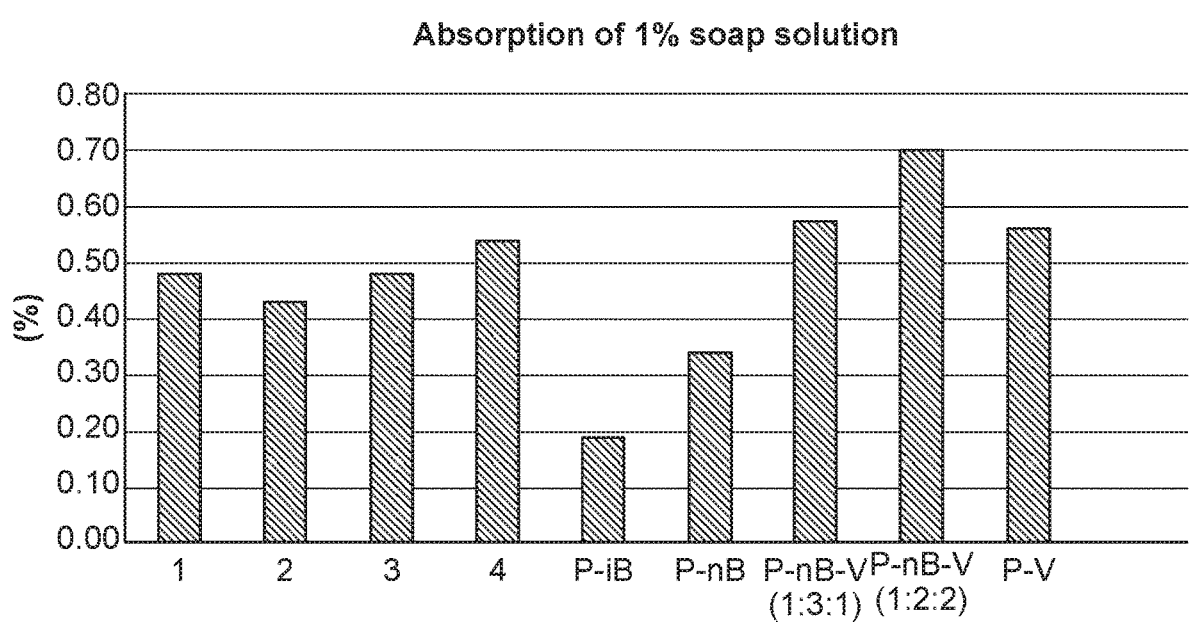
FIG. 6 is a graphical representation of absorporation and extraction of 1% soap solution after 1 day.

The results are presented in FIGS. 5A; 5B and 6.

Yellowness

The yellowness observed during the test period (40 min) was significantly lower in the PVC sheets plasticised with the polyolesters from Example 1 and 2 compared to the PVC sheets plasticised with DINCH, DOP, DPHP and DINP.

DPHP—1, DOP—2, DINP—3, DINCH—4

The fusion time for the plasticisers according to the present invention was found to be shorter in comparison to certain commercially available plasticisers 1-4. See FIG. 1.

Figure 2:
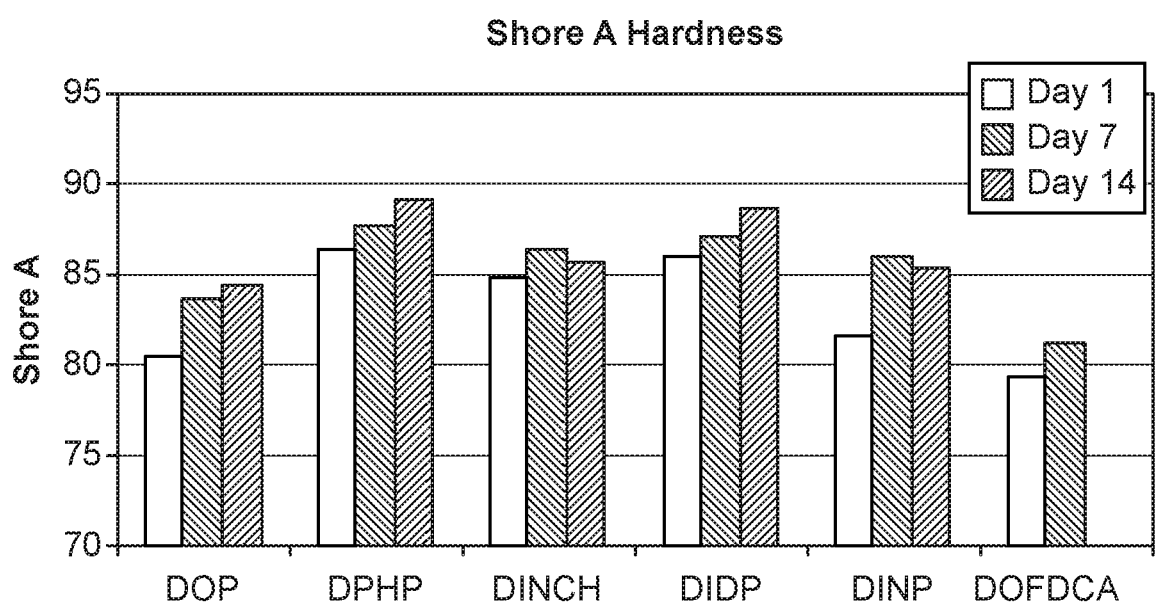
FIG. 2 is a graphical representation of ShoreA Hardness for various plasticizers at each of Day 1, Day 7 and Day 14 at room temperature and 50% relative humidity.

The plasticising effect of the plasticisers according to the present invention was found to be high in comparison to commercially available plasticisers 1-4. This means that lower amounts of plasticiser can be added with maintained hardness. See. FIG. 2.

Especially the plasticisers P-iB and P-V according to the invention showed very good migration values in FIG. 4A. The comparative example, TMP-V showed to be poor due to its high migration value.

Especially the plasticiser P-V according to the invention showed very good volatility value in FIG. 4B. The comparative example TMP-V showed to be poor due to its high volatility.

The invention claimed is:

1. A thermoplastic article suitable for use in environments where it is exposed to heat, wherein the thermoplastic article is based on a low-emitting plasticized polyvinylchloride composition comprising at least 20%, by weight of pentaerythritol tetravalerate and having a fusion time of less than 5.50 s and a volatility of less than 10% weight loss produced by mixing pentaerythritol tetravalerate with a polyvinylchloride composition, said fusion time being measured according to DIN 54 802 and ISO/DIS 4574 and said volatility being measured according to ISO 176 Method A.

2. The thermoplastic article of claim 1, wherein the plasticized polyvinylchloride composition comprises at least 30% by weight of pentaerythritol tetravalerate.

3. The thermoplastic article of claim 1, wherein the plasticized polyvinylchloride composition also comprises an oligo ester of 2-ethylhexanol and furandicarboxylic acid.

4. The thermoplastic article of claim 1, wherein the plasticized polyvinylchloride composition also comprises pentaerythritol adipate.

5. The thermoplastic article according to claim 1, wherein said article is a foil, film or molded polyvinylchloride article.

6. The thermoplastic article according to claim 2, wherein said article is a foil, film or molded polyvinylchloride article.

7. The thermoplastic article according to claim 3, wherein said article is a foil, film or molded polyvinylchloride article.

8. The thermoplastic article according to claim 4, wherein said article is a foil, film or molded polyvinylchloride article.

9. The thermoplastic article according to claim 1, wherein said article is a low-fogging dashboard for cars.

10. The thermoplastic article according to claim 2, wherein said article is a low-fogging dashboard for cars.

11. The thermoplastic article according to claim 3, wherein said article is a low-fogging dashboard for cars.

12. The thermoplastic article according to claim 4, wherein said article is a low-fogging dashboard for cars.

13. A method for producing a low-emitting plasticised polyvinylchloride composition, having a fusion time of less than 5.50 s and a volatility of less than 10% weight loss, by mixing pentaerythritol tetravalerate with a polyvinylchloride composition, said fusion time being measured according to DIN 54 802 and ISO/DIS 4574 and said volatility being measured according to ISO 176 Method A.

14. The method according to claim 13, wherein said plasticized polyvinylchloride composition comprises at least 20% by weight of pentaerythritol tetravalerate.

15. The method according to claim 13, wherein said plasticized polyvinylchloride composition comprises at least 30% by weight of pentaerythritol tetravalerate.

16. The method according to claim 13, wherein said plasticized polyvinylchloride composition also comprises an oligo ester of 2-ethylhexanol and furandicarboxylic acid.

17. The method according to claim 13, wherein said plasticized polyvinylchloride composition also comprises pentaerythritol adipate.

* * * * *